(12) United States Patent
King et al.

(10) Patent No.: US 9,937,437 B2
(45) Date of Patent: Apr. 10, 2018

(54) FRACTIONATION SYSTEM HAVING RECTIFYING AND STRIPPING COLUMNS IN A SINGLE VESSEL WITH A UNIFORM DIAMETER

(71) Applicant: UOP LLC, Des Plaines, IL (US)

(72) Inventors: Stephen T. King, Villa Park, IL (US); Steven Kozup, Chicago, IL (US); Xin X. Zhu, Long Grove, IL (US)

(73) Assignee: UOP LLC, Des Plaines, IL (US)

( * ) Notice: Subject to any disclaimer, the term of this patent is extended or adjusted under 35 U.S.C. 154(b) by 1055 days.

(21) Appl. No.: 14/041,645

(22) Filed: Sep. 30, 2013

(65) Prior Publication Data

US 2015/0052941 A1    Feb. 26, 2015

Related U.S. Application Data

(60) Provisional application No. 61/869,462, filed on Aug. 23, 2013.

(51) Int. Cl.
| | |
|---|---|
| *B01D 3/14* | (2006.01) |
| *B01D 3/20* | (2006.01) |
| *C07C 7/04* | (2006.01) |
| *B01D 19/00* | (2006.01) |

(52) U.S. Cl.
CPC ............ *B01D 3/143* (2013.01); *B01D 3/141* (2013.01); *B01D 19/0015* (2013.01); *C07C 7/04* (2013.01); *B01D 3/14* (2013.01); *B01D 3/20* (2013.01)

(58) Field of Classification Search
CPC .......... B01D 3/14; B01D 3/141; B01D 3/143; B01D 3/20; C07C 11/06; C07C 9/10; C07C 9/12

USPC ...................................... 208/355; 203/78, 79
See application file for complete search history.

(56) References Cited

U.S. PATENT DOCUMENTS

| | | | |
|---|---|---|---|
| 2,108,659 A | | 2/1938 | Dunham |
| 3,412,016 A | * | 11/1968 | Graven ................. B01D 3/141 196/102 |
| 4,275,255 A | | 6/1981 | Vora |
| 4,559,108 A | * | 12/1985 | Ahlberg ............... B01D 1/2806 202/154 |
| 6,250,106 B1 | * | 6/2001 | Agrawal ................ B01D 3/14 62/643 |
| 6,417,420 B1 | * | 7/2002 | Stewart ................. B01D 3/141 585/323 |
| 2003/0181772 A1 | * | 9/2003 | Meyer ................... B01D 3/141 585/324 |
| 2010/0331589 A1 | | 12/2010 | Zimmermann et al. |
| 2012/0271080 A1 | | 10/2012 | Sechrist et al. |
| 2013/0131417 A1 | | 5/2013 | Werba et al. |

FOREIGN PATENT DOCUMENTS

CN    102603457 A    7/2012

OTHER PUBLICATIONS

Porter, E.A., "Distillation", Thermopedia, Feb. 10, 2011, http://www.thermopedia.com/content/703/.*
EP Search Report dated Feb. 13, 2017 for corresponding EP Application No. 14838536.

* cited by examiner

*Primary Examiner* — Jonathan Miller
*Assistant Examiner* — Jonathan Luke Pilcher

(57) ABSTRACT

Fractionation systems utilizing a single rectifying column with a stripping column housed in the same vessel and having a uniform diameter are described. Methods of separating feed streams using the fractionation systems are also described.

10 Claims, 7 Drawing Sheets

FRACTIONATION SYSTEM HAVING RECTIFYING AND STRIPPING COLUMNS IN A SINGLE VESSEL WITH A UNIFORM DIAMETER

BACKGROUND OF THE INVENTION

Olefin hydrocarbons are valued for the production of a variety of materials, including many petrochemicals. In some dehydrogenation processes, short chain saturated hydrocarbons are modified to form a corresponding olefin. A particularly useful olefin is propylene, which is produced by dehydrogenation of propane. Propylene is an enormously useful petrochemical commodity with demand steadily growing. Propylene is used in the production of polypropylene, acrylonitrile, acrylic acid, acrolein, and many others useful compounds. Polypropylene is widely used in many consumer and industrial products.

Propane dehydrogenation processes that produce olefins such as propylene may include feeding propane to a dehydrogenation unit where it is dehydrogenated using a catalyst to form propylene. A compressor compresses the effluent from the dehydrogenation unit to a high pressure to recover unreacted propane and propylene in a recovery section. The compressed reactor effluent is chilled to maximize propane and propylene recovery.

The hydrocarbon product stream may be communicated from the recovery unit to a de-ethanizer distillation column where ethane and lighter components are recovered as an overhead gas, and propane and propylene, and heavy boiling compounds are removed as bottoms. These bottoms are then communicated to a propylene splitter distillation column where propylene is recovered as an overhead liquid and unreacted propane from the bottoms may be recycled back to the dehydrogenation unit.

These processes often require significant energy input to boil, pressurize and otherwise process the various steps. The significant energy demands lead to high costs and other disadvantages.

SUMMARY OF THE INVENTION

One aspect of the invention is a fractionation system. In one embodiment, the fractionation system includes a rectifying column having a feed inlet between a top and a bottom plate, a reflux inlet at the top plate, a fluid inlet at the bottom plate, an overhead product outlet at the first plate, and a bottoms outlet at the bottom plate; a rectifying column side reboiler in communication with the rectifying column; a stripping column having a fluid inlet at a top plate, an overhead outlet at the top plate, and a bottoms outlet at the bottom plate, the bottoms outlet of the rectifying column being in fluid communication with the fluid inlet of the stripping column, the overhead outlet of the stripping column being in fluid communication with the fluid inlet of the rectifying column; a stripping column reboiler in communication with the stripping column; and the rectifying column and the stripping column being in a single vessel having a uniform diameter, the rectifying column being positioned above the stripping column.

Another aspect of the invention is a process of separating a feed stream. In one embodiment, the process includes introducing the feed stream into a fractionation system comprising a rectifying column and a stripping column, the rectifying column and the stripping column being in a single vessel having a uniform diameter, the rectifying column being positioned above the stripping column, the feed stream being introduced into a feed inlet of the rectifying column, the feed inlet between a top plate and a bottom plate, the rectifying column having a reflux inlet at the top plate, a fluid inlet at the bottom plate, an overhead product outlet at the first plate, and a bottoms outlet at the bottom plate. The feed stream is separated in the rectifying column into an overhead product stream and a bottoms stream. The bottoms stream from the rectifying column is introduced into a fluid inlet in the stripping column, the feed inlet at the top of the stripping column, the stripping column having an overhead outlet at the top plate, and a bottoms outlet at the bottom plate. The bottoms stream from the rectifying column is separated into an overhead stream and a bottoms stream in the stripping column. The overhead stream from the stripping column is introduced into the fluid inlet of the rectifying column. A portion of the overhead product stream from the rectifying column is refluxed to the reflux inlet of the rectifying column. At least a portion of the bottoms stream from the rectifying column is reheating reheated in a rectifying column reboiler, and at least a portion of the bottoms stream from the stripping column is reheated in a stripping column reboiler.

DETAILED DESCRIPTION OF THE INVENTION

A fractionation system has been developed which utilizes a single rectifying column with a stripping column housed in the same vessel and having a uniform diameter. This arrangement reduces the capital and operating costs compared to a system with two rectifying columns or a single swaged vessel containing the rectifying and stripping columns.

The fractionation system also simplifies the control and operation of the fractionation because there is only one reflux line instead of two.

In considering various invention embodiments illustrated herein, it will be appreciated that the invention will find utility in applications for production of olefins from paraffins in general and is not limited to propylene production. Significant utility exists, however, when invention embodiments are practiced with propylene with the result that corresponding example embodiments have been selected for illustration herein.

Figure 1:
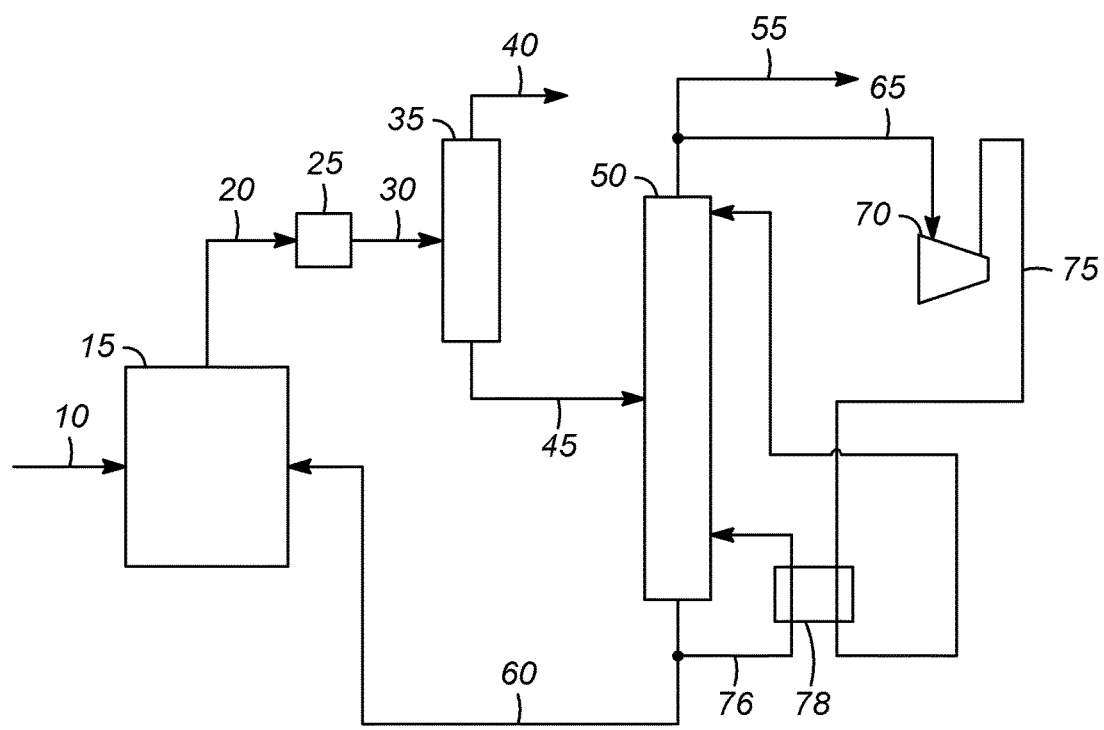
FIG. 1 illustrates one embodiment of a process for producing propylene.

Referring now to the Figures, FIG. 1 is a schematic of one example of a prior art process for producing propylene. Feed stream 10 is fed to a distillation section 15 where contaminants in the feed stream 10 are removed. The feed stream 10 may contain various components, with one example being at least 95% propane (wt), with impurities including ethane, and butanes. A distillation section output stream 20, which may be predominantly propane, is communicated to a reactor 25, where it is reacted with a catalyst to produce propylene. The reactor effluent may be chilled to enhance hydrocarbon recovery (not illustrated).

A reactor output stream 30 containing propylene (with some ethane and potentially other impurities) is communicated to a de-ethanizer column 35 where impurities such as hydrogen, methane, ethane, and ethylene are removed as the overhead vapor 40. The product propylene and unreacted propane are taken as a de-ethanizer bottoms stream 45 to an olefin splitter 50. A splitter overhead stream 55 contains a high percentage of propylene. A splitter bottoms stream 60 containing unreacted propane and at least some heavy boiling components is recycled back to the distillation section 15 for removal of the heavy boiling components.

An additional splitter output stream 65 containing at least some, and in some cases as much as 100% vapor phase propylene is compressed in a heat pump compressor 70 (which may be referred to for convenience as "HPC 70"). The HPC output stream 75 heats a portion 76 of splitter bottoms stream 60 in heat exchanger 78 and is recycled to the splitter 50.

Figure 2:
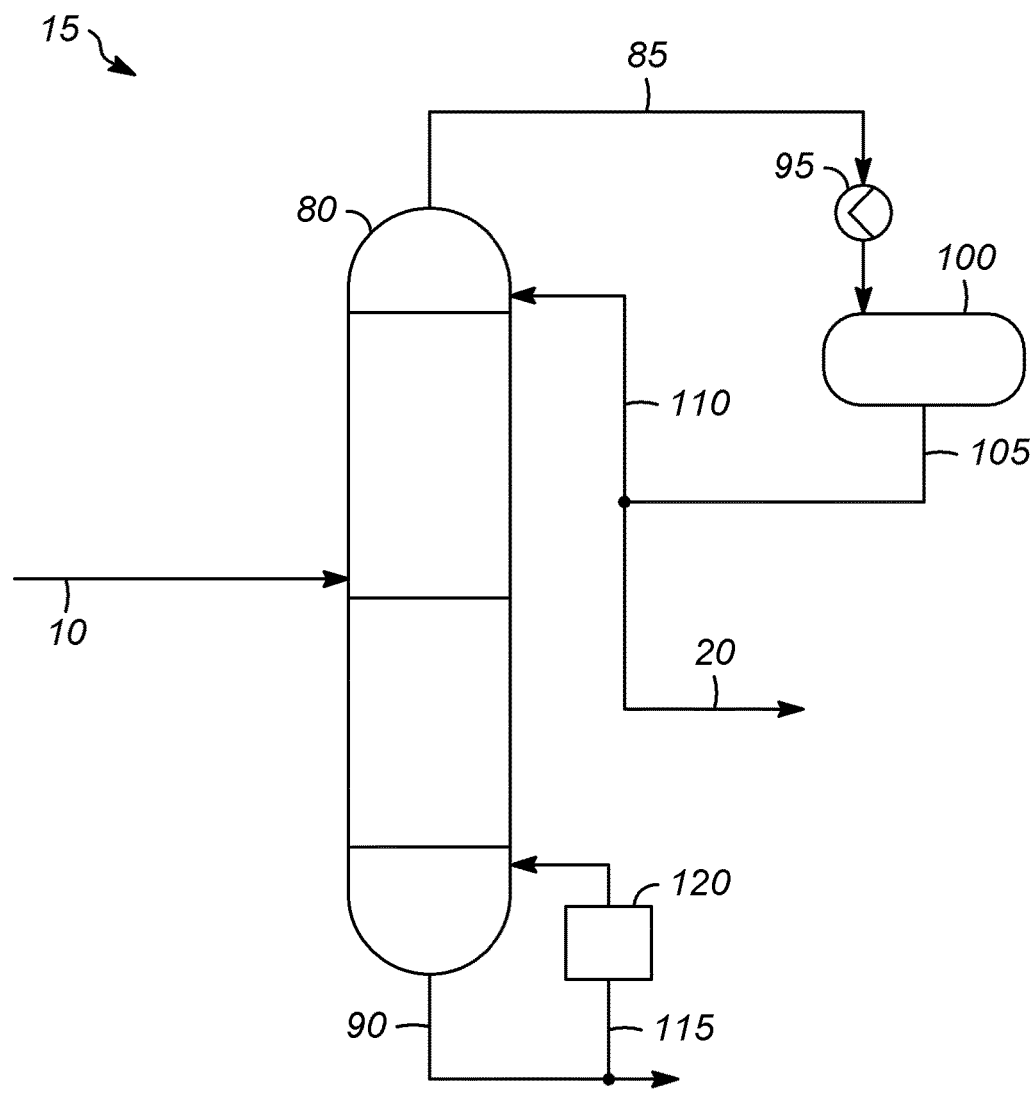
FIG. 2 illustrates one embodiment of a distillation section used in the process of FIG. 1.

FIG. 2 shows one embodiment of a prior art distillation section 15. The feed stream 10 is fed to a depropanizer column 80 where it is separated into an overhead stream 85 and a bottoms stream 90. The overhead stream 85 is cooled in a heat exchanger 95 and sent to a column overhead receiver (or accumulator) 100. Condensed stream 105 is separated into reflux stream 110 which is sent to the depropanizer column 80 and distillation section output stream 20.

A portion 115 of the bottoms stream 90 is reheated in a steam reboiler 120 and returned to the depropanizer column 80.

In prior art systems such as this, it is desirable to achieve as high a rate of recovery as possible in the distillation column; the recycle and bottoms streams should be as low as possible in unreacted fuel (e.g., propane). In many prior art methods and systems, recovery rates exceeding 99% were disclosed, with the result that recycle and bottom streams included less than 1% unreacted fuel (e.g., propane).

Figure 3:
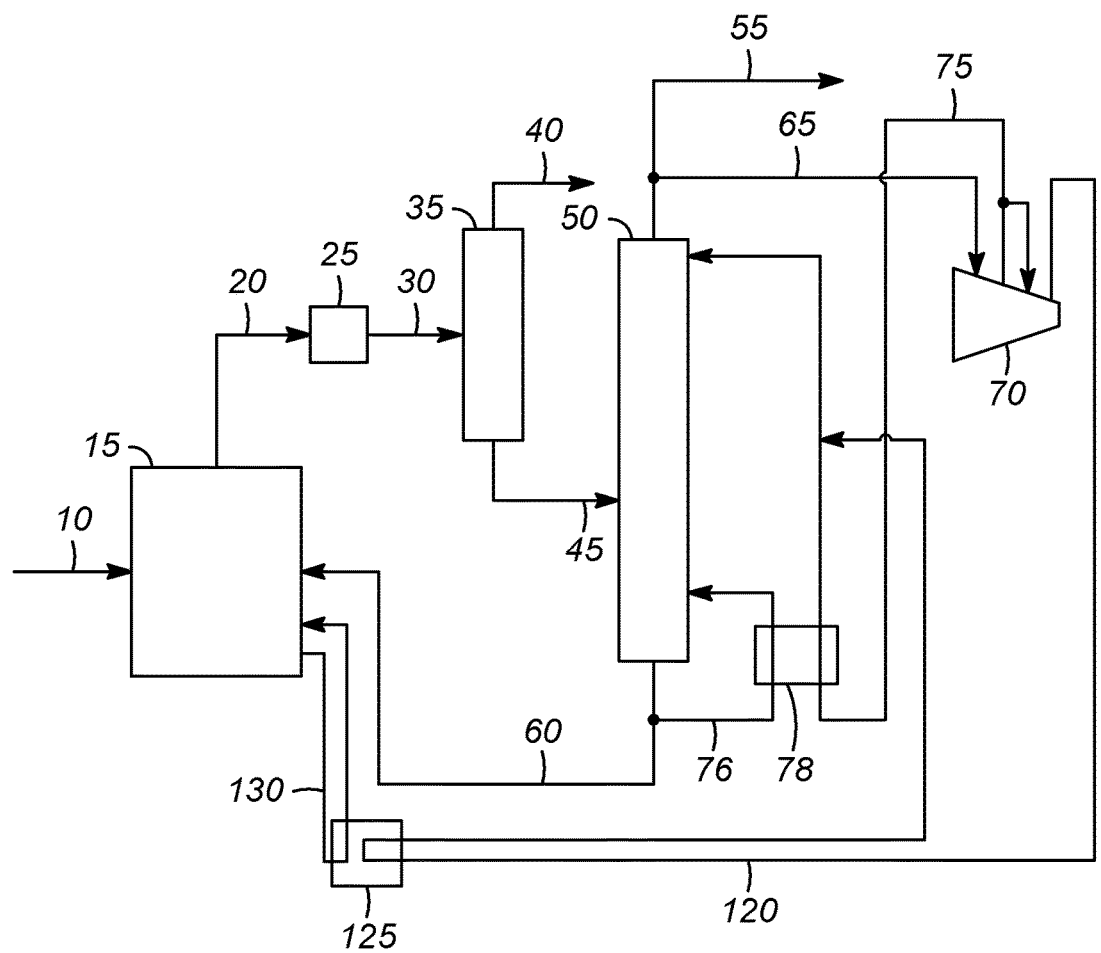
FIG. 3 illustrates another embodiment of a process for producing propylene.

In some prior art systems and methods, heat pump compressors such as HPC 70 produce excess heat that is lost to the environment. FIG. 3 illustrates an embodiment of a distillation section 15 designed to capture the excess heat through an HPC second output stream 120 which is put to valuable use through reboiler 125, as described in US Publication No. 2013/0131417, which is incorporated herein by reference. Important advantages, efficiencies and cost savings are thereby achieved.

In this embodiment, a higher pressure and temperature HPC second output stream 120 is communicated to a distillation section heat exchanger 125 where it is used to heat a distillation section stream 130 that includes unreacted propane. Heat exchanger 125, as well as other heat exchangers discussed herein, may be of any conventional design, with one example being a counter-flow tube-in-shell design and another example using high heat transfer technologies such as Highflux™ (available from UOP, Des Plaines, Ill.) or plate type exchangers. In some (but not all) embodiments, the heat exchanger 125 may be a reboiler, and may be referred to herein in some embodiments as such. The HPC second output stream 120 may then be communicated back to the splitter 50 as reflux (as illustrated) or may be communicated to other components such as a propylene collection tank (not illustrated).

Figure 4:
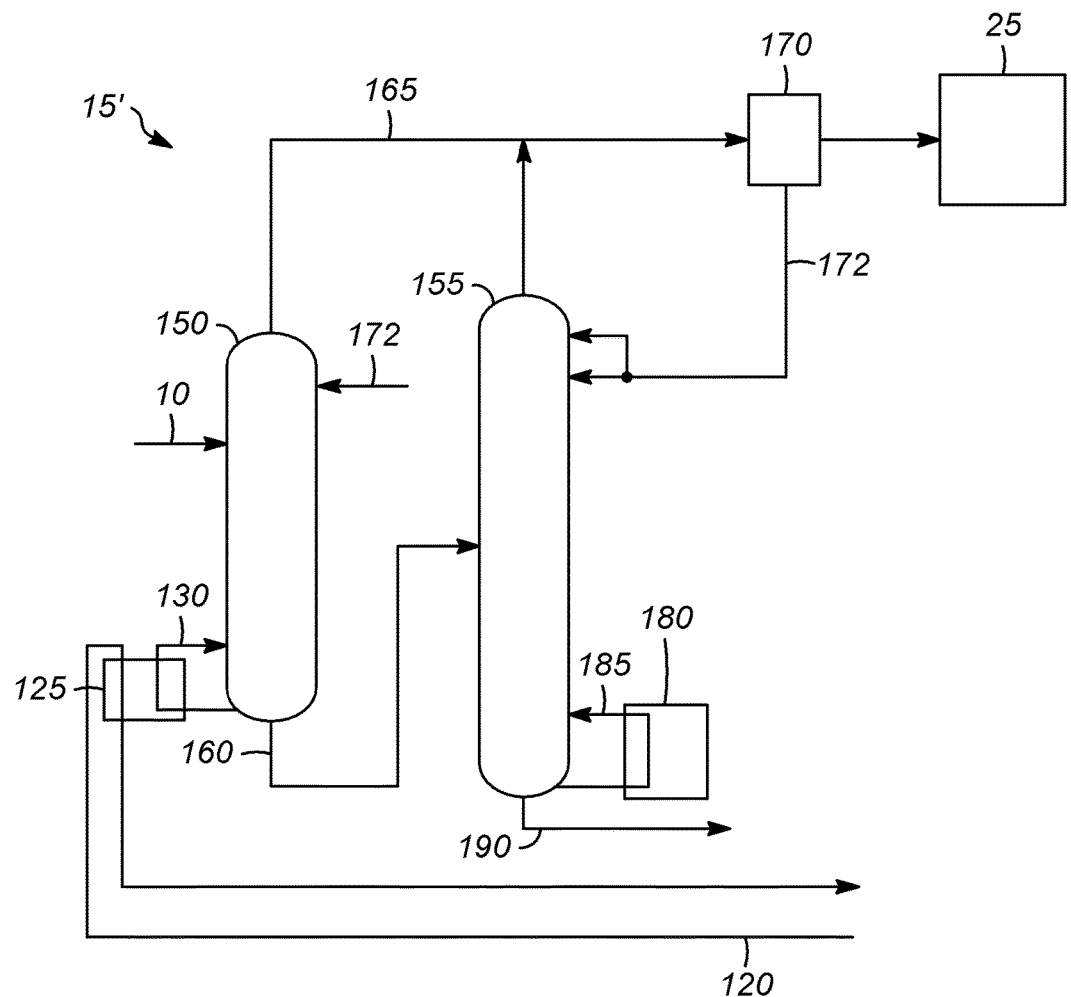
FIG. 4 illustrates one embodiment of a distillation section used in the process of FIG. 3.

In one example of this embodiment of distillation section 15' as shown in FIG. 4, there are first and second columns 150 and 155 arranged in series. In some embodiments, these columns may be referred to as depropanizer columns reflecting their purpose of conditioning propane to be suitable feed for reactor 25. The feed stream 10 containing propane and other hydrocarbons is fed to the first distillation column 150 where high boiling components are recovered at the first distillation column bottoms stream 160, and the propane is recovered in first distillation column overhead stream 165 and communicated through a heat exchanger 170 for cooling and then sent to reactor 25. Stream 172 is sent to first and second columns 150 and 155 as reflux.

The first distillation column bottoms stream 160 containing some propane as well as heavier boiling hydrocarbons is then communicated into the second distillation column 155 for recovery of the propane and concentration of the high boiling hydrocarbons.

The first distillation column bottoms stream 160 has been illustrated as a bottom streams from the first distillation column 150. It will be appreciated, however, that this first distillation column bottoms stream 160 could be extracted from the first distillation column 150 at different locations as desired, and therefore that the use of the term "bottoms stream" is for convenience only and is not intended to limit the scope of the invention. This likewise applies to other uses of "bottoms" herein when made in this context.

A distillation column overhead stream 175 from the second distillation column 155 containing a high proportion of propane is combined with the first distillation column overhead stream 165 and communicated to the reactor 25. A second distillation column reboiler 180 heats a second distillation column bottom recycle stream 185. A second distillation column bottoms stream 190 containing heavier components is removed for use as desired.

Designing first and second distillation columns 150 and 155 in this manner allowed for exploitation of heat from the HPC 70 (FIG. 3) that in the prior art was lost to the environment. The first distillation column reboiler 125 extracts heat from the HPC second output stream 120 to heat a first distillation column recycle stream 130. First distillation column 150 and HPC 70 (FIG. 3) have been designed so that the boiling point of first distillation column recycle stream 130 is lower than the temperature of the HPC second output stream 120 to make this feasible. This may be accomplished in many different particular configurations by varying operating temperatures, pressures, flow rates, propane recovery in first distillation column 150, number of stages or trays in first and second distillation columns 150 and 155, and other parameters. Some design parameters have been discovered, however, that are believed to provide particularly useful benefits and advantages.

For example, the first distillation column 150 was designed and operated so that the boiling point of the first distillation column recycle stream 130 was no more than about 60° C. The first distillation column recycle stream 130 (as well as first distillation column bottoms stream 160, which is generally consistent in quality to that of recycle stream 130) also contained a significant amount of unreacted propane, which in some embodiments is at least about 5% (by wt). The lower recovery amounts in this system were used to ensure that heat from the HPC second output stream 36 could be exploited. This can also be expressed in terms of the difference in quality of first distillation column recycle stream 130, as well as first distillation column bottoms stream 160 as compared to second distillation column bottom stream 190. In some embodiments, it was useful to operate with the first distillation column bottoms stream 160/first distillation recycle stream 130 having a boiling point that was at least 20° C. lower than that of the second distillation column bottoms stream 190.

The quality of the first distillation column bottoms recycle stream 130 can affect the desired pressure level, and thereby, energy efficiency of using the HPC second output stream 120 for this purpose. Design parameters include exchanger design, flow rate, and temperature differential between first distillation column recycle stream 130 boiling point and HPC second output stream 120 temperature. In many situations, it was useful to maintain a temperature differential between first distillation column recycle stream 130 boiling point and HPC second output stream 120 temperature (with HPC second output stream 120 being hotter than first distillation column recycle stream 130) of at least 5° C. to ensure that heat from the HPC second output stream 120 could be used to reheat the first distillation column recycle stream 130. In some embodiments, the HPC second output stream 120 is compressed to a pressure of at least about 25 kg/m². When compressed to 30 kg/m², the HPC second output stream 120 in some embodiments had a condensation temperature of about 68° C., making it useful as a heat source for recycle streams having boiling points below about 60° C.

The bottoms stream 190 of the second distillation column 155 is generally consistent with bottoms streams from single distillation columns. It has a much lower unreacted propane content than the bottoms stream 160 from the first distillation column 150 and correspondingly higher concentration of longer chain hydrocarbons, with a boiling point of 100° C. or more. Low or even medium pressure steam or other suitable heated medium may accordingly be required by the second distillation column reboiler 180.

In one embodiment, the first column was specified with 56 trays to recover 10% of the $C_3$ material in the net bottoms and to maintain 100 mppm of $nC_4+C_{4=}$ (normal butane and $C_4$ olefin) in the overhead vapor. The second column had 67 trays and was specified to recover 0.5% of the $C_3$ material feed to the depropanizer system in the net bottoms while maintaining the 100 mppm of $nC_4+C_{4=}$ in the overhead vapor. Together, the depropanizer system recovers 99.5% of $C_3$ material in the net overhead with 100 mppm of $nC_4+C_{4=}$ net overhead purity. The two column system allows a lower first column bottoms temperature so it can be reboiled with the heat pump compressor second stage (HPC2) discharge.

Although FIG. 4 illustrates two distillation columns 150 and 155 arranged in series, three or more columns could be used in other embodiments.

However, the capital and operating costs for two large depropanizer columns are high. It would be desirable to reduce the capital costs, or the operating costs, and preferably both for the distillation section.

A fractionation system was developed with a rectifying column and a stripping column in the same vessel, as described in U.S. Application Ser. No. 61/869,483, entitled FRACTIONATION SYSTEM AND METHOD INCLUDING RECTIFYING COLUMN AND STRIPPING COLUMN, filed on even date herewith, which is incorporated herein by reference.

Figure 5:
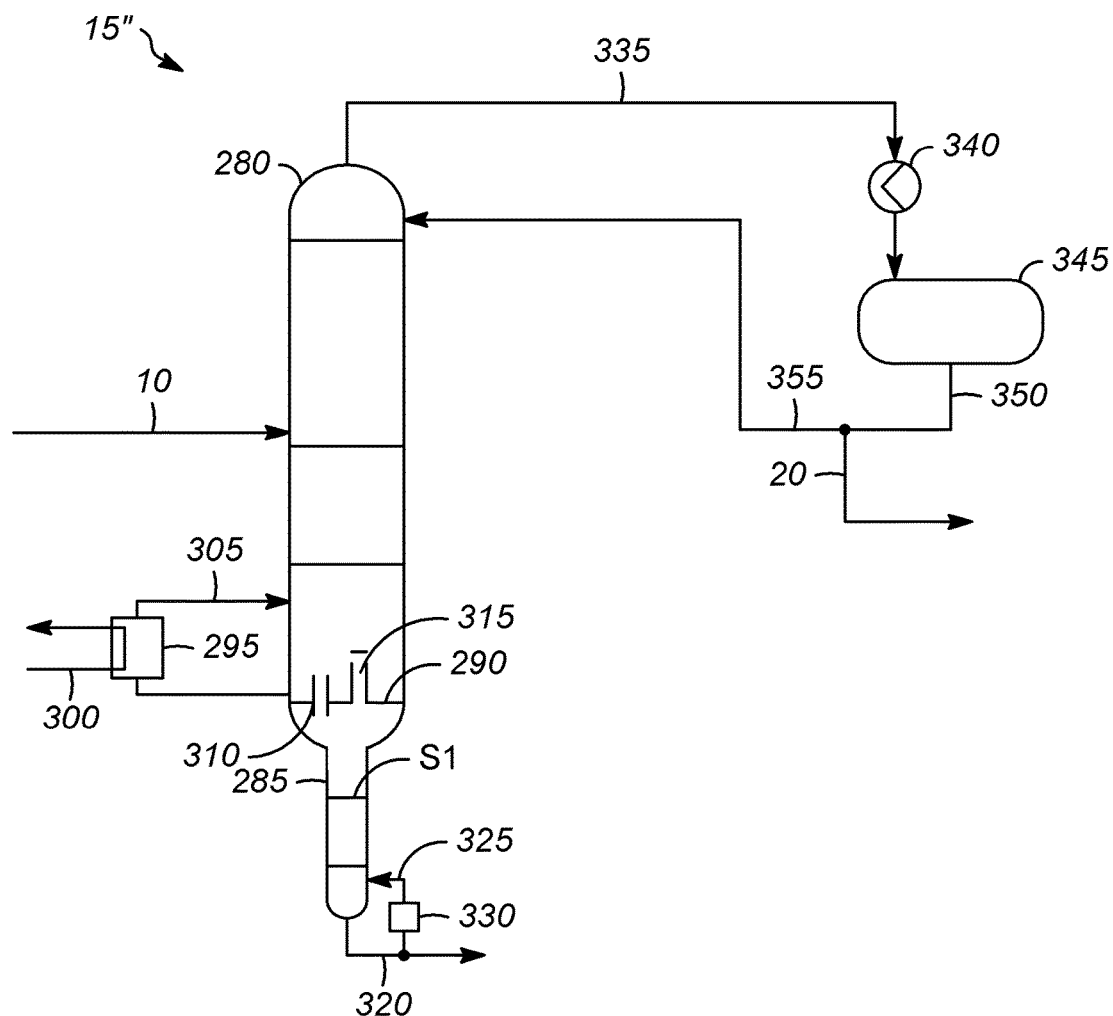
FIG. 5 illustrates one embodiment of a distillation section which can be used in the process of FIG. 3.

In this arrangement, as illustrated in FIG. 5, the stripping column 285 is stacked underneath the rectifying column 280 in a swaged arrangement. A liquid accumulator tray 290 separates the rectifying column 280 from the stripping column 285.

Feed 10 is introduced into the rectifying column 280.

The overhead stream 335 from the rectifying column 280 is cooled in a heat exchanger 340 and sent to a column overhead receiver 345. Condensed stream 350 is separated into a reflux stream 255 which is sent to the rectifying column 280 and distillation section output stream 20.

Liquid from the liquid accumulator tray 290 flows through the downcomer 310 into tray S1 of the stripping column 285, and vapor from tray S1 flows up through vapor riser 315 of the liquid accumulator tray 295 into the bottom of the rectifying column 280.

The rectifying column reboiler 295 feeds off the liquid accumulator tray 290. HPC second output stream 300 is used to heat recycle stream 305. The inlet and outlet for recycle stream 305 are in the space between the bottom tray of the rectifying column 280 and the liquid accumulator tray 290.

Stripping column bottoms stream 320 containing heavier components is removed. Recycle stream 325 is heated in steam reboiler 330 and returned to the stripping column 285.

The rectifying column bottoms temperature can be specified to keep the log mean temperature difference (LMTD) and duty of the heat recovery reboiler equal to allow the discharge pressure of the HPC2 to be within an economical range.

The stripping column is specified so that the fractionation system maintains the 99.5% recovery of $C_3$ material in the net overhead required for propane dehydrogenation processes. To achieve this recovery, the stripping column bottoms temperature is set at 104.4° C. (220° F.) with a depropanizer overhead pressure of 1.765 MPa (g) (256 psig). This allows the stripping column to remove or strip out the $C_3$ material from the heavy $C_{4+}$ material so the valuable $C_3$ material can be sent back to the rectifying column as vapor. The 104.4° C. (220° F.) temperature is in the range for 276 kPa (g) (40 psig) steam as the heating medium for the stripping column reboiler. For example, the rectifying column could be sized for sieve trays with a column diameter of 13', while the stripping column could be sized with sieve trays with a column diameter of 5'. Column tray counts and rectifying column feed location can be optimized to achieve the minimal utility consumption.

However, swaged columns are more expensive to manufacture than columns having the same diameter throughout because of the cone section between the two sections and the increased wind moment. Therefore, it would be desirable to have a column with the same diameter for both the rectifying and stripping sections. The challenge is how to design the column internals to accommodate a single diameter for both sections.

A single diameter was achieved by using trays which allowed a reduction in the diameter of the rectifying column and trays which allowed an increase in the diameter of the stripping column.

Figure 6:
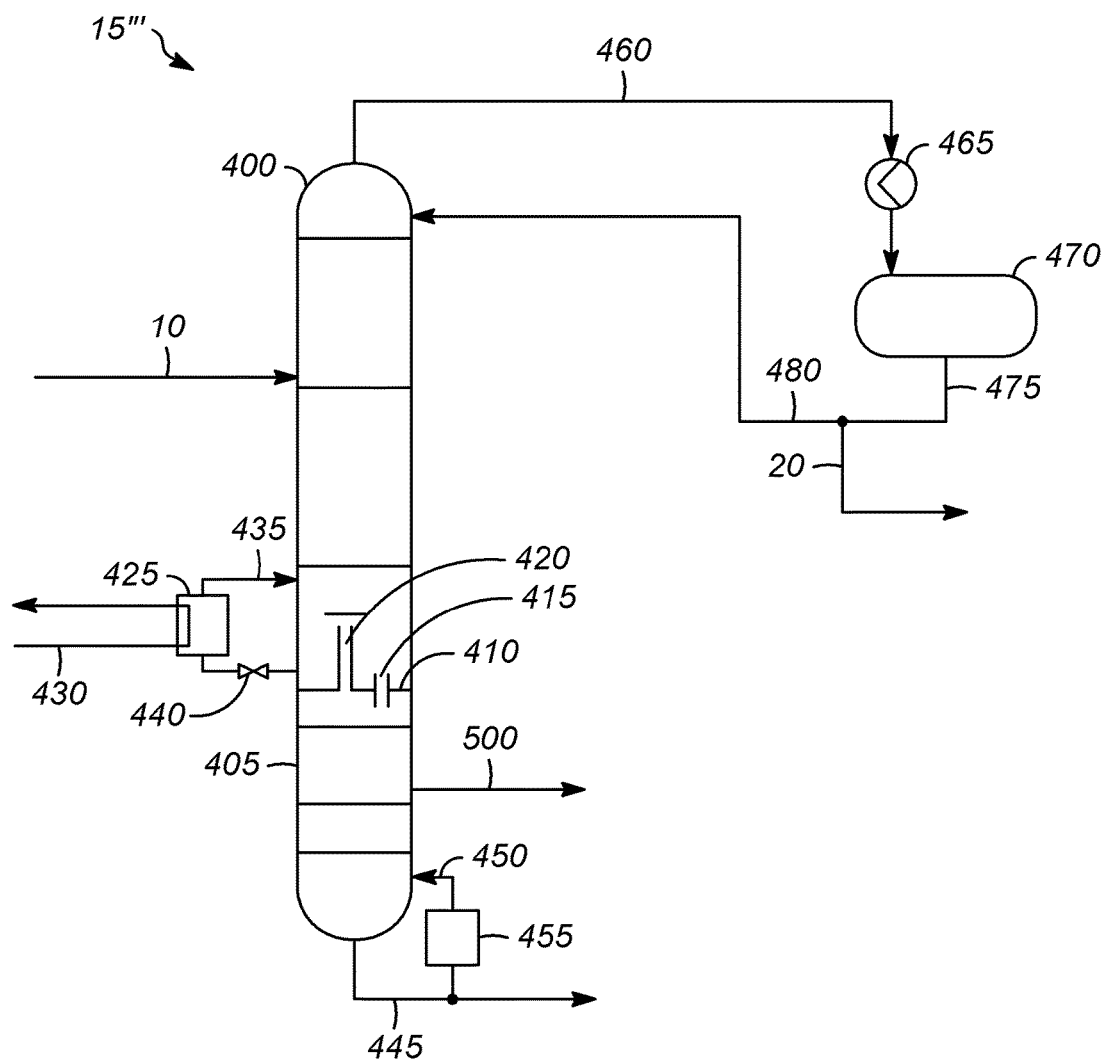
FIG. 6 illustrates one embodiment of a distillation section of the present invention which can be used in the process of FIG. 3.

In one embodiment shown in FIG. 6, the trays in the rectifying column 400 and stripping column 405 extend across the column. The diameter of the rectifying column 400 determines the overall vessel diameter.

The trays in the rectifying column 400 are high performance trays. The high performance trays can accommodate more vapor and liquid than conventional trays. Suitable high performance trays include, but are not limited to, MD™ trays, ECMD™ trays, and SimulFlow™ Trays (available from UOP LLC) and other high performance or increased capacity trays.

There is a liquid accumulator tray 410 separating the rectifying column 400 and the stripping column 405. The liquid accumulator tray 410 has a downcomer 415 to allow liquid to flow into the stripping column 405, and a vapor riser 420 to allow vapor to flow up into the rectifying column 400. The liquid accumulator tray is designed with sufficient liquid residence time (e.g., a 30 second residence time) for the process reboiler inlet to stabilize the vaporization. Additionally, the bottom of the reboiler return nozzle 305 will be above the liquid level of the accumulator tray to allow for adequate vapor/liquid disengagement of the return line (e.g., about 45.7 cm (18 in) above the liquid level of the accumulator). Also, the top of the reboiler return nozzle will be below the top of the vapor riser height so that no liquid from the reboiler return will spill down the vapor riser (e.g., about 30.5 cm (12 in) below the top of the vapor riser height). The distance between the top of the vapor riser and the tray above the accumulator tray will be about equal to the tray spacing in the column section above the accumulator tray (typically about 45.7-61.0 cm (18-24 in)). The total vapor riser area will be sufficient so that the stripping column vapor can be channeled and evenly distributed into the rectifying column with minimal pressure drop (e.g., about 20% of the total column cross-sectional area). The reboiler inlet draw nozzle will be located in a sump (e.g., the sump can be 1.5 times the pipe diameter of the draw nozzle in height, width, and depth). The reboiler inlet line will typically be flush with the bottom of the sump to provide a liquid seal in the reboiler inlet line. The distance between the sump and the tray below will be about equal to the tray spacing (typically about 45.7-61.0 cm (18-24 in)).

The stripping column 405 is designed with a design margin to accommodate about 40% of the reboiling duty in the event there is a deficit of heat input from the process reboiler. The trays are designed for the increased load, and valve trays will allow enough turndown for the desired heat input from the rectifying column reboiler.

The trays in the stripping column 405 are designed with larger downcomers than normal and with a reduced number of valves to accommodate the diameter needed for the rectifying column 400. They can be any type of conventional trays. Suitable trays for the stripping column include, but are not limited to, valve, and sieve trays.

The rectifying column reboiler 425 is located slightly above the bottom head of the rectifying column 400 to allow draining of the reboiler lines into the sump for startup and shutdown. The rectifying column reboiler 425 feeds off the liquid accumulator tray 410. HPC second output stream 430 is used to heat recycle stream 435. The rectifying column reboiler inlet and outlet for recycle stream 435 are in the space between the bottom tray of the rectifying column 400 and the liquid accumulator tray 410, with the rectifying column reboiler outlet positioned above the rectifying column reboiler inlet. Typically, the reboiler inlet line is a sump that is about 1.5 pipe diameters deep. This allows liquid from the accumulator tray deck to free drain into the inlet line.

An inlet throttling valve 440 is provided on the rectifying column reboiler inlet line to allow the reboiler to be located at a lower level than required for 33% vaporization. This valve will regulate the reboiler circulation and reduce the cost of elevating the reboiler to a higher level than the lower part of the vessel.

Stripping column bottoms stream 445 containing heavier components is removed. Recycle stream 450 is heated in steam reboiler 455 and returned to the stripping column 405.

The overhead stream 460 from the rectifying column 400 is cooled in a heat exchanger 465 and sent to column overhead receiver 470. Condensed stream 475 is separated into a reflux stream 480 sent to the rectifying column 400 and distillation section output stream 20.

Figure 7:
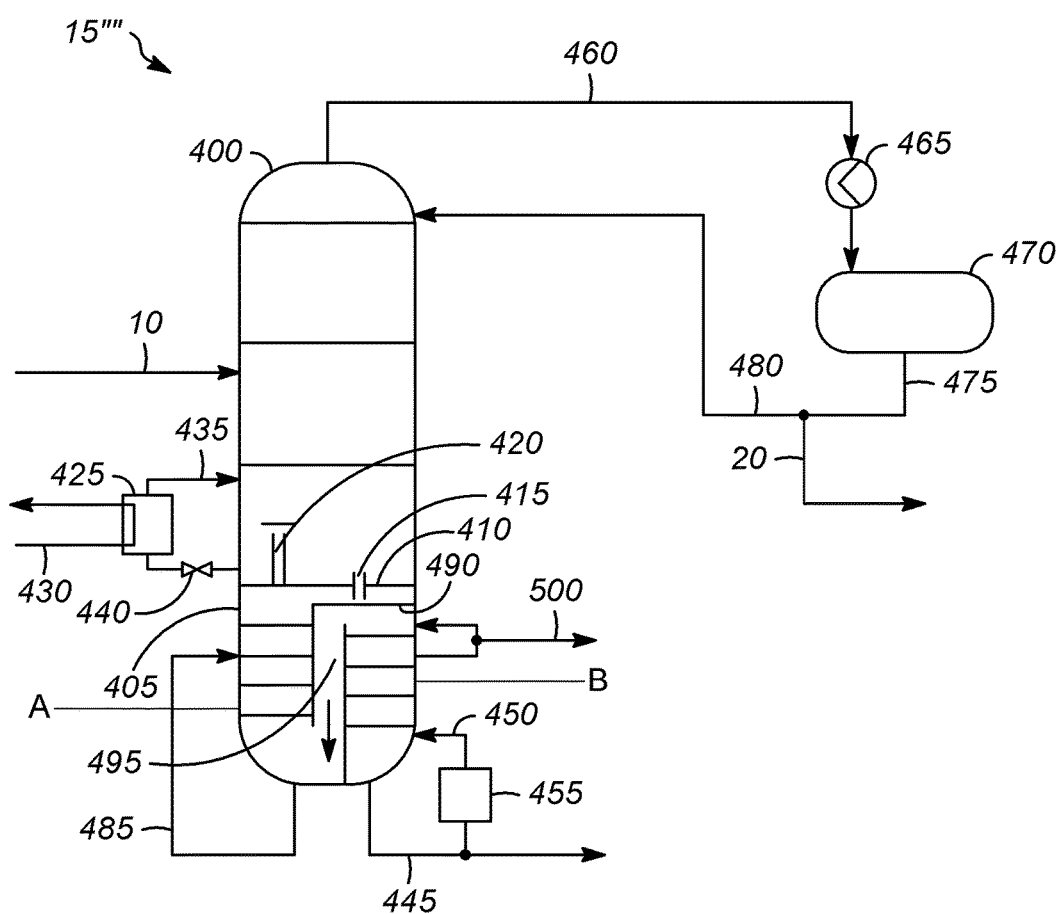
FIG. 7 illustrates another embodiment of a distillation section of the present invention which can be used in the process of FIG. 3.

In another embodiment shown in FIG. 7, the trays in the stripping column 405 each cover about half of the stripping column 405. They are arranged side by side in two stacks A and B in the stripping column 405, which reduces the height of the stripping column 405.

The liquid from the liquid accumulator tray 410 flows through the downcomer 415 onto the top tray of the stripping column 405. It flows down through the trays in stack A. The liquid 485 is then pumped to the top tray in stack B, and it flows down through the trays in stack B. Vapor flows up from the bottom of stack B to the top. A blind tray 490 at the top of stack B prevents any vapor/liquid communication from the top of stack B to rectifying column 400. The vapor is sent through vapor channel 495 to the bottom of stack A. It flows upward through stack A and out the vapor riser 420 between the stripping column 405 and the rectifying column 400 where it combines with the vapor from the rectifying column reboiler.

A portion of the liquid 485 being pumped to the top of stack B can be withdrawn as a side draw 500 of heavies, if desired.

The rectifying column and stripping column of this embodiment can utilize any type of trays.

The rectifying column was designed to maintain a 30% recovery of $C_3$ material in the rectifying column net bottoms stream being sent to the stripping column. This allows the temperature in the bottoms to be about 56° C. and about 96% $C_3$ material (molar basis). This is ideal temperature and composition for the rectifying column bottoms so that the heat pump compressor discharge stream (e.g., about 86° C.) can be used to reboil the rectifying column and allow condensation of the heat pump material at the outlet of the hot side of the reboiler (e.g., about 67° C.). Thus, the rectifying column reboiler will transfer the heat from the heat pump compressor discharge stream to the rectifying column. This is feasible since the thermodynamic properties of $C_3$ material are similar. The rectifying column bottoms will be slumped to the stripping column where the $C_3$ material will be stripped out and the heavy $C_{4+}$ material will be concentrated. The temperature of the stripping column bottoms will be fixed at 104° C. which will strip out the $C_3$ material from the heavier $C_{4+}$ material. The $C_3$ material will be returned to the bottom section of the rectifying column. The $C_3$ vapor stream provides additional stripping vapor to the rectifying column and aids in fractionation of the rectifying column.

The rectifying column 400 was designed and operated so that the bubble point of the rectifying column recycle stream 435 was no more than about 60° C. The rectifying column recycle stream 435 also contained a significant amount of unreacted propane, which in some embodiments is at least about 5% (by wt). The lower recovery amounts in this system were used to ensure that heat from the HPC second output stream 430 could be utilized to reboil the material in the depropanizer rectifying column The composition of the rectifying column bottoms recycle stream 435 and the HPC second output stream 430 can affect the heat pump compressor utility consumption, and thereby, the feasibility of using the HPC second output stream 430 for this purpose. Design parameters include exchanger design, flow rate, and temperature differential between rectifying column recycle stream 435 bubble point and HPC second output stream 430 temperature. It is useful to maintain a log mean temperature difference (LMTD) within the rectifying column reboiler 425 of greater than 5° C. between HPC second output stream 430 and the rectifying column reboiler inlet stream 435. This is to allow for adequate heat exchange within the reboiler and allow the cold side of the reboiler (rectifying side) to vaporize and the hot side (or heat pump side) to condense). In some embodiments, the HIPC second output stream 430 is compressed to a pressure of at least about 3 MPa (g) (30 bar(g)). When compressed to 3 MPa (g) (30 bar(g)), the HPC second output stream 430 in some embodiments had a condensation temperature of about 68° C., making it useful as a heat source to reboil liquids with bubble points near 60° C.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A fractionation system comprising:
a rectifying column having a feed inlet between a top and a bottom plate, a reflux inlet at the top plate, a fluid inlet at the bottom plate, an overhead product outlet at the first plate, and a bottoms outlet at the bottom plate;
a rectifying column side reboiler in communication with the rectifying column through a reboiler return nozzle, the reboiler return nozzle having a bottom and a top;
a stripping column having a fluid inlet at a top plate, an overhead outlet at the top plate, and a bottoms outlet at the bottom plate, the bottoms outlet of the rectifying column being in fluid communication with the fluid inlet of the stripping column, the overhead outlet of the stripping column being in fluid communication with the fluid inlet of the rectifying column;
a stripping column reboiler in communication with the stripping column;
the rectifying column and the stripping column being in a single vessel having a uniform diameter, the rectifying column being positioned above the stripping column, the rectifying column and the stripping column each containing trays extending across the diameter;
a liquid accumulator tray positioned between the rectifying column and the stripping column providing fluid and vapor communication between the rectifying column and the stripping column, the liquid accumulator tray having a downcomer and a vapor riser, said vapor riser having a top; and
wherein the top of the reboiler return nozzle is positioned below the top of the vapor riser.

2. A fractionation system comprising:
a rectifying column having a feed inlet between a top and a bottom plate, a reflux inlet at the top plate, a fluid inlet at the bottom plate, an overhead product outlet at the first plate, and a bottoms outlet at the bottom plate;
a rectifying column side reboiler in communication with the rectifying column through a reboiler return nozzle, the reboiler return nozzle having a bottom and a top;
a stripping column having a fluid inlet at a top plate, an overhead outlet at the top plate, and a bottoms outlet at the bottom plate, the bottoms outlet of the rectifying column being in fluid communication with the fluid inlet of the stripping column, the overhead outlet of the stripping column being in fluid communication with the fluid inlet of the rectifying column;
a stripping column reboiler in communication with the stripping column;
the rectifying column and the stripping column being in a single vessel having a uniform diameter, the rectifying column being positioned above the stripping column, the rectifying column containing trays extending across the diameter and the stripping column having a side-by-side stacked arrangement of fractionation trays, wherein the bottom of the first stack is in liquid communication with the top of the second stack and wherein the top of the second stack is in vapor communication with the bottom of the first stack;
a liquid accumulator tray positioned between the rectifying column and the stripping column providing fluid and vapor communication between the rectifying column and the stripping column, the liquid accumulator tray having a downcomer and a vapor riser, said vapor riser having a top; and
wherein the top of the reboiler return nozzle is positioned below the top of the vapor riser.

3. The fractionation system of claim 2 wherein the vapor communication is provided by a vapor channel from the top of the second stack to the bottom of the first stack.

4. The fractionation system of claim 1 further comprising a condenser having an inlet in fluid communication with the product overhead outlet of the rectifying column, and an outlet in fluid communication with the reflux inlet of the rectifying column.

5. The fractionation system of claim 1 wherein at least a portion of a heat source for the rectifying column side reboiler is a stream from a heat pump compressor.

6. The fractionation system of claim 5 wherein the heat pump compressor is in fluid communication with a splitter column, the splitter column being downstream of a reactor, the reactor being in fluid communication with the overhead product outlet of the rectifying column.

7. The fractionation system of claim 5 wherein the rectifying column reboiler further comprises a valve to control an inlet flow to the rectifying column side reboiler.

8. The fractionation system of claim 1 wherein the overhead product outlet of the rectifying column is in fluid communication with a reactor.

9. The fractionation system of claim 1 wherein the overhead product outlet of the rectifying column is above the top plate of the rectifying column, the reflux inlet of the rectifying column is above the top plate of the rectifying column and below the overhead product outlet, the overhead outlet of the stripping column is above the top plate of the stripping column, the fluid inlet of the stripping column is above the top plate of the stripping column and below the overhead outlet of the stripping column, and the fluid inlet of the rectifying column is below the bottom plate of the rectifying column and above the bottoms outlet of the rectifying column.

10. The fractionation system of claim 2 wherein there is a blind tray at the top of the second stack to prevent direct liquid and vapor communication between the second stack and the rectifying column.

* * * * *